United States Patent
Lehrman et al.

(10) Patent No.: US 6,864,796 B2
(45) Date of Patent: Mar. 8, 2005

(54) SYSTEMS WITHIN A COMMUNICATION DEVICE FOR EVALUATING MOVEMENT OF A BODY AND METHODS OF OPERATING THE SAME

(75) Inventors: Michael L. Lehrman, Washington, DC (US); Alan R. Owens, Longmont, CO (US); Michael E. Halleck, Longmont, CO (US); Edward L. Massman, Dallas, TX (US)

(73) Assignee: iLife Solutions, Inc., Dallas, TX (US)

( * ) Notice: Subject to any disclaimer, the term of this patent is extended or adjusted under 35 U.S.C. 154(b) by 0 days.

(21) Appl. No.: 10/331,958

(22) Filed: Dec. 30, 2002

(65) Prior Publication Data

US 2003/0146844 A1 Aug. 7, 2003

Related U.S. Application Data

(63) Continuation of application No. 09/727,974, filed on Nov. 30, 2000, now Pat. No. 6,501,386, which is a continuation-in-part of application No. 09/396,991, filed on Sep. 15, 1999, now Pat. No. 6,307,481.

(51) Int. Cl.[7] .............................................. G08B 23/00
(52) U.S. Cl. .............................. 340/573.1; 340/539.11; 340/669; 340/426.15; 340/670; 464/566; 600/300; 600/301
(58) Field of Search .............................. 340/573.1, 669, 340/670, 539.1, 426, 539.11, 426.15; 464/566; 600/300, 301

(56) References Cited

U.S. PATENT DOCUMENTS

| | | | |
|---|---|---|---|
| 3,614,763 A | 10/1971 | Yannuzzi | |
| 4,110,741 A | 8/1978 | Hubert et al. | |
| 4,284,986 A | 8/1981 | Amortegui | |
| 4,292,630 A | 9/1981 | Dumont | |

(List continued on next page.)

Primary Examiner—Jeffery Hofsass
Assistant Examiner—Tai T. Nguyen

(57) ABSTRACT

The present invention introduces systems, as well as methods of operating such systems, within a communication device for evaluating movement of a body relative to an environment. According to an exemplary embodiment, the system comprises a sensor and a processor. The sensor, which is associable with the body, is operable to repeatedly sense accelerative phenomena of the body. The processor, which is associated with the sensor, is operable to process the sensed accelerative phenomena as a function of at least one accelerative event characteristic. The system, and, more particularly, the processor generates state indicia relative the environment, and determines whether the evaluated body movement is within environmental tolerance. In a preferred embodiment, the processor communicates various state indicia to a monitoring controller, preferably using at least one of a wired network and a wireless network. The monitoring controller cooperates with the processor to remotely monitor the body.

20 Claims, 9 Drawing Sheets

U.S. PATENT DOCUMENTS

| | | |
|---|---|---|
| 4,536,755 A | 8/1985 | Holzgang et al. |
| 4,617,525 A | 10/1986 | Lloyd |
| 4,829,285 A | 5/1989 | Brand et al. |
| 4,858,622 A | 8/1989 | Osterweil |
| 4,972,177 A | 11/1990 | Nolan |
| 5,008,654 A | 4/1991 | Callaway |
| 5,038,137 A | 8/1991 | Lloyd |
| 5,045,839 A | 9/1991 | Ellis et al. |
| 5,146,206 A | 9/1992 | Callaway |
| 5,209,343 A | 5/1993 | Romano et al. |
| 5,300,921 A | 4/1994 | Hoch et al. |
| 5,398,019 A | 3/1995 | Barnett et al. |
| 5,402,107 A | 3/1995 | Rencavage |
| 5,430,435 A | 7/1995 | Hoch et al. |
| 5,477,211 A | 12/1995 | Reynolds |
| 5,523,742 A | 6/1996 | Simkins et al. |
| 5,554,975 A | 9/1996 | Hall et al. |
| 5,694,340 A | 12/1997 | Kim |
| 5,751,214 A | 5/1998 | Cowley et al. |
| 5,879,309 A | 3/1999 | Johnson et al. |
| 5,917,414 A * | 6/1999 | Oppelt et al. ............ 340/573.1 |
| 5,941,836 A | 8/1999 | Friedman |
| 5,957,957 A | 9/1999 | Sheldon |
| 6,129,686 A | 10/2000 | Friedman |
| 6,501,386 B2 * | 12/2002 | Lehrman et al. ............ 340/669 |
| 6,540,674 B2 * | 4/2003 | Zadrozny et al. ........... 600/300 |

* cited by examiner

X FILTER

Y FILTER

X FILTER

Y FILTER

SYSTEMS WITHIN A COMMUNICATION DEVICE FOR EVALUATING MOVEMENT OF A BODY AND METHODS OF OPERATING THE SAME

This application is a continuation of prior U.S. Application Ser. No. 09/727,974 filed on Nov. 30, 2000, now issued as U.S. Pat. No. 6,501,386 on Dec. 31, 2002, which is a continuation-in-part of U.S. Application Ser. No. 09/396,991 filed Sep. 15, 1999, now U.S. Pat. No. 6,307,481.

RELATED APPLICATIONS

The present invention is related to that disclosed in United States patent application Ser. No. 09/542,197 filed Apr. 4, 2000 by Halleck et al. entitled "Apparatus and Method for Detecting An Inclination of A Body." The related patent application is commonly assigned to the assignee of the present invention. The disclosure of the related patent application is hereby incorporated by reference in the present patent application as if fully set forth herein.

TECHNICAL FIELD OF THE INVENTION

The present invention relates generally to means for detecting body movement, and, more particularly, relates to systems, and methods of operation thereof, within a communication device for evaluating movement of a body relative to an environment.

BACKGROUND OF THE INVENTION

Methods for determining specific movements of a body that use a variety of devices, apparatus and systems are, generally speaking, known. The term "body" is defined broadly hereafter and includes both organic and inorganic objects.

In point of fact, many methods are known for sensing body movement, or non-movement (i.e., sensed dynamic accelerations, including cessation of movement), as well as, for sensing body movement over time, which is commonly used to determine comparative levels of activity of a monitored body (See, U.S. Pat. Nos. 4,110,741, 4,292,630, 5,045, 839, and 5,523,742). These methodologies, however, merely report various levels of body activity, and, simply stated, fail to recognize possible causes for any increased or decreased level of body activity.

In contrast, other methodologies have developed over time for the detection of falls (See also, U.S. Pat. Nos. 4,829,285, 5,477,211, 5,554,975, and 5,751,214). These methodologies are largely based upon the utilization of one or more mechanical switches (e.g., mercury switches) that determine when a body has attained a horizontal position. These methods however fail to discern "normal," or acceptable, changes in levels of body activity. Stated another way, the foregoing fall detection methodologies provide no position change analysis and, therefore, cannot determine whether a change in position, once attained, is acceptable or unacceptable.

Various training methods have been conceived for sensing relative tilt of a body (See, U.S. Pat. Nos. 5,300,921 and 5,430,435), and some such methodologies have employed two-axis accelerometers. The output of these devices, however, have reported only static acceleration of the body (i.e., the position of a body relative to earth within broad limits). It should be appreciated that static acceleration, or gravity, is not the same as a lack of dynamic acceleration (i.e., vibration, body movement, and the like), but is instead a gauge of position. While accelerometers that measure both static and dynamic acceleration are known, their primary use has heretofore been substantially confined to applications directed to measuring one or the other, but not both.

Thus, it may be seen that the various conventional detectors fall into one of two varieties, those that gauge movement of the body and those that gauge a body's position by various means, with neither type capable of evaluating body movement to determine whether the same is normal or abnormal; and if abnormal, whether such movement is so abnormal to be beyond tolerance, for instance, to be damaging, destructive, crippling, harmful, injurious, or otherwise alarming or, possibly, distressing to the body. None of the methodologies heretofore known have provided a suitable means to evaluate body movement over time and to determine whether such movement is tolerable. Further improvement could thus be utilized.

The general use of communication devices has greatly increased over the last few years. Communication devices comprise cellular telephones, personal digital assistants, hand held computers, laptops, computers, wireless Internet access devices, and other similar types of communications equipment. The number of such communication devices in use is steadily increasing.

It would be very useful to have a communications device that is capable of evaluating movement of a body relative to an environment. For example, when a communications device detects a body movement that signifies the occurrence of a potentially dangerous event (e.g., a fall), the communication device can immediately send an alarm to call for assistance.

SUMMARY OF THE INVENTION

To address the above-introduced deficiencies of the prior art, the present invention introduces systems, as well as methods of operating such systems, within a communication device for evaluating movement of a body relative to an environment. For the purposes hereof, the term "body" is defined broadly, meaning any organic or inorganic object whose movement or position may suitably be evaluated relative its environment in accordance with the principles hereof; and where the term "environment" is defined broadly as the conditions and the influences that determine the behavior of the physical system in which the body is located. The term "communication device" is defined broadly to include, without limitation, cellular telephones, personal digital assistants, hand held computers, laptops, computers, wireless Internet access devices, and other similar types of communications equipment.

An advantageous embodiment of a system that evaluates movement of a body relative to an environment in accordance herewith includes both a sensor and a processor. In operation, the sensor is associated with the body and operates to repeatedly sense accelerative phenomena of the body. The processor, which is associated with the sensor, processes the sensed accelerative phenomena as a function of at least one accelerative event characteristic to determine whether the evaluated body movement is within environmental tolerance. The processor also preferably generates state indicia while processing the sensed accelerative phenomena, which represents the state of the body within the environment over time.

For the purposes hereof, the term "sensor" is defined broadly, meaning a device that senses one or more absolute values, changes in value, or some combination of the same, of at least the sensed accelerative phenomena. According to a preferred embodiment, described in detail hereafter, the sensor may be a plural-axis sensor that senses accelerative phenomena and generates an output signal to the processor indicative of both measurements of both dynamic and static acceleration of the body in plural axes.

According to this embodiment, the processor receives and processes the output signal. The processor is preferably programmed to distinguish between normal and abnormal accelerative events, and, when an abnormal event is identified, to indicate whether the abnormal event is tolerable, or within tolerance. In further embodiments, the processor may be programmed to distinguish other physical characteristics, including temperature, pressure, force, sound, light, relative position, and the like.

It should be noted that the relevant environment may be statically or dynamically represented. The sophistication of any such representation may be as complex or as uncomplicated as needed by a given application (e.g., disability, injury, infirmity, relative position, or other organic assistance monitoring; cargo or other transport monitoring; military, paramilitary, or other tactical maneuver monitoring; etc.). It should further be noted that any representation may initially be set to, or reset to, a default, including, for instance, a physically empty space, or vacuum.

Regardless, the principles of the preferred exemplary embodiment discussed heretofore require at least one accelerative event characteristic to be represented to enable the processor to determine whether the evaluated body movement is within environmental tolerance, which is again advantageously based upon both dynamic and static acceleration measurements.

According to a related embodiment, the processor is further operable, in response to processing the sensed accelerative phenomena, to generate state indicia, which includes tolerance indicia, generated in response to determining whether the evaluated body movement is within environmental tolerance. Preferably, such tolerance indicia is compared with at least one threshold, likely associated with the accelerative event characteristic. In response to such comparison, the processor controls a suitable indicating means to initiate an alarm event; to communicate such tolerance indicia to a monitoring controller; to generate statistics; or the like.

According to a related preferred embodiment, the system may be associated with other components or sensing systems. For instance, in an assistance monitoring application, the sensor may repeatedly sense dynamic and static acceleration of the body in the plural axes and generate output signals indicative of the measurements. The processor continuously processes the output signals to distinguish between selected accelerative and non-selected accelerative events (described in detail hereafter) based upon both the dynamic and the static acceleration of the body, and generates state indicia, including tolerance indicia, that is communicated to a remote monitoring controller. The tolerance indicia is communicated to the monitoring controller for record keeping/statistical purposes, as well as to provide "live" monitoring of the individual subscriber.

Communication between the processor and the controller may be by a wireless network, a wired network, or some suitable combination of the same, and may include the Internet. Preferably, the system generates an alert whenever the monitored subscriber is in "jeopardy," as determined by the system, such as in response to a debilitating fall by the subscriber. In a further embodiment, the processor is operable to repeatedly generate "heartbeat" indicia that indicates that the system is in an operable state, whereby absence of the same informs the monitoring controller that some other part of the system is malfunctioning.

In an alternate embodiment of the present invention, the sensor and the processor may both be located within a communications device. The communications device may communicate by a wireless network, a wired network, or some suitable combination of the same, and may include the Internet.

The foregoing has outlined rather broadly the features and technical advantages of the present invention so that those skilled in the art may better understand the DETAILED DESCRIPTION OF THE INVENTION that follows. Additional features and advantages of the invention will be described hereinafter that form the subject of the claims of the invention. Those skilled in the art should appreciate that they may readily use the conception and specific embodiments disclosed as a basis for modifying or designing other structures for carrying out the same purposes of the present invention. Those skilled in the art should also realize that such equivalent constructions do not depart from the spirit and scope of the invention in its broadest form.

Before undertaking the DETAILED DESCRIPTION OF THE INVENTION, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, and the term "associable" may mean to include, be included within, interconnect with, contain, be contained within, connect to or with, couple to or with, be communicable with, cooperate with, interleave, juxtapose, be proximate to, be bound to or with, have, have a property of, or the like; and the terms "controller" and "processor" mean any device, system or part thereof that controls at least one operation, such a device may be implemented in hardware, firmware or software, or some suitable combination of at least two of the same. It should be noted that the functionality associated with any particular controller/processor may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present invention, and the advantages thereof, reference is now made to the following descriptions taken in conjunction with the accompanying drawings, wherein like numbers designate like objects, and in which.

DESCRIPTION OF THE INVENTION

Figure 1:
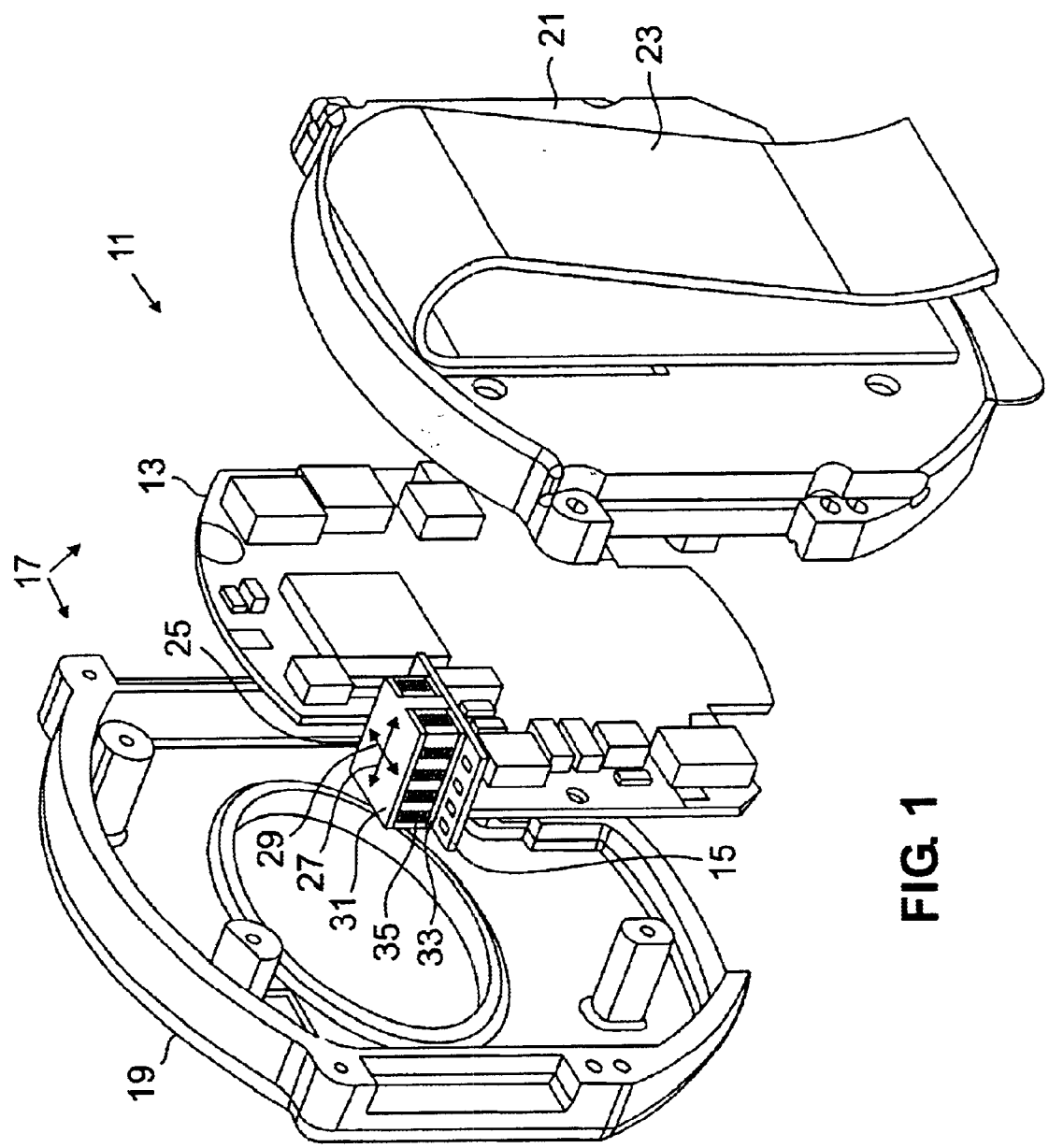
FIG. 1 illustrates an isometric view of an exemplary embodiment of a system that evaluates body movement in accordance with the principles of the present invention.

Turning initially to FIG. 1, there is illustrated an isometric view of an exemplary embodiment of a system (generally designated 11) that evaluates body movement in accordance with the principles of the present invention, and more particularly that measures and distinguishes selected accelerative events of a body (not shown). As used in this disclosure, the phrases "accelerative events" or "accelerative phenomena" are defined as occurrences of change in velocity of the body (or acceleration), whether in magnitude, direction or both.

System 11 includes circuit boards 13 and 15 (connected boards at right angles to one another) that are associated with a housing (generally designated 17) utilizing known mounting techniques. Exemplary housing 17 (and system 11, for that matter), when assembled, is approximately one centimeter thick and is approximately five centimeters across in any direction.

Housing 17 may comprise, for example, exemplary housing halves 19 and 21 that encase boards 13 and 15, although those skilled in the art will understand that any configuration suitable for a particular implementation of the invention may be arranged.

Exemplary rear half 21, is provided with a clip 23 for associating system 11 with the body (e.g., people, animals, objects of various sorts, etc.). Exemplary clip 23 is shown as a mechanical spring-type clip, but could be any known attachment device or system, including either mechanical or chemical attachment systems, or any other suitable means for associating system 11 with the body.

System 11 includes a processor (shown in FIG. 2) and a sensor 25. Exemplary sensor 25 operates to sense accelerative phenomena of the body, and is mounted on circuit board 13 with x and y axes 27 and 29, respectively, oriented thereat (though other orientations could be utilized).

Sensor 25 is illustratively shown as a plural-axis (dual shown) acceleration measuring device suitably mounted on a single monolithic integrated circuit (one conventional sensor is an accelerometer available from ANALOG DEVICES, INC., located at One Technology Way, Norwood, Mass., United States of America, namely, Model No. ADXL202). Sensor 25 includes polysilicon surface-micromachined sensor layer 31 built on top of silicon wafer 33. Polysilicon springs 35 resiliently suspend sensor layer 31 over the surface of wafer 33 providing resistance against acceleration forces. Deflection of the sensor layer is measured using a differential capacitor formed by independent fixed and central plates, the fixed plates driven by 180° out of phase square waves having amplitude proportional to acceleration. Signal outputs from each axis of sensor 25 are conditioned (i.e., phase sensitive demodulation and low pass filtering) and presented at analog output nodes. While not utilized in the primary advantageous embodiment of this invention, the ANALOG DEVICES' accelerometer is operable to convert the analog signals to duty cycle modulated ("DCM") signals at a DCM stage providing digital output signals capable of being directly counted at a processor.

While techniques for reconstructing analog signals from the digital output signals may suitably be utilized (e.g., passing the duty cycle signals though an RC filter), thereby allowing use of the digital signal output of a sensor of system 11 hereof, use of the analog signal outputs has been found advantageous due to the increased bandwidth availability (0.01 Hz to 5 kHz, adjustable at capacitors at the output nodes to bandlimit the nodes implementing low-pass filtering for antialiasing and noise reduction), and the measuring sensitivity that may be attained. A typical noise floor of five hundred micro "g" per Hertz ($500 \times 10^{-6}$ "g"/Hz) is achieved, thereby allowing signals below five milli "g" ($5 \times 10^{-3}$ "$\mu$g") to be resolved for bandwidths below 60 Hz. The value "g" is the acceleration of gravity at the surface of the earth (32 feet/sec$^2$ or 9.8 m/sec$^2$).

According to the illustrated embodiment, sensor 25 generates analog output voltage signals corresponding to measurements in the x and y axes, which include both an ac voltage component proportional to G forces (i.e., dynamic acceleration component related to vibrations of sensor layer 31) and a dc voltage component proportional to an angle relative to earth (i.e., static acceleration component related to gravity). This open loop acceleration measurement architecture, capable of measuring both static and dynamic acceleration, can thus be utilized to determine position of a body by measuring both the x and y output voltages simultaneously, as well as measure forces of impact experienced by a body. This information comprises state indicia, and utilizing both signal components from both outputs, the sensed accelerative phenomena of the body may subsequently be processed to distinguish a variety of accelerative phenomena and, ultimately, to selectively act based on the distinctions, as is described in detail hereafter to determine whether the evaluated body movement is normal or abnormal, and, if abnormal, whether the same is within tolerance.

It is noted that the foregoing embodiment has been introduced for illustrative purposes only. In alternate embodiments, any sensor that is capable of sensing accelerative phenomena relative to a body may be used in lieu of, or even in conjunction with, sensor 25. Further, alternate orientations of sensor 25 may be used for different applications.

Figure 2:
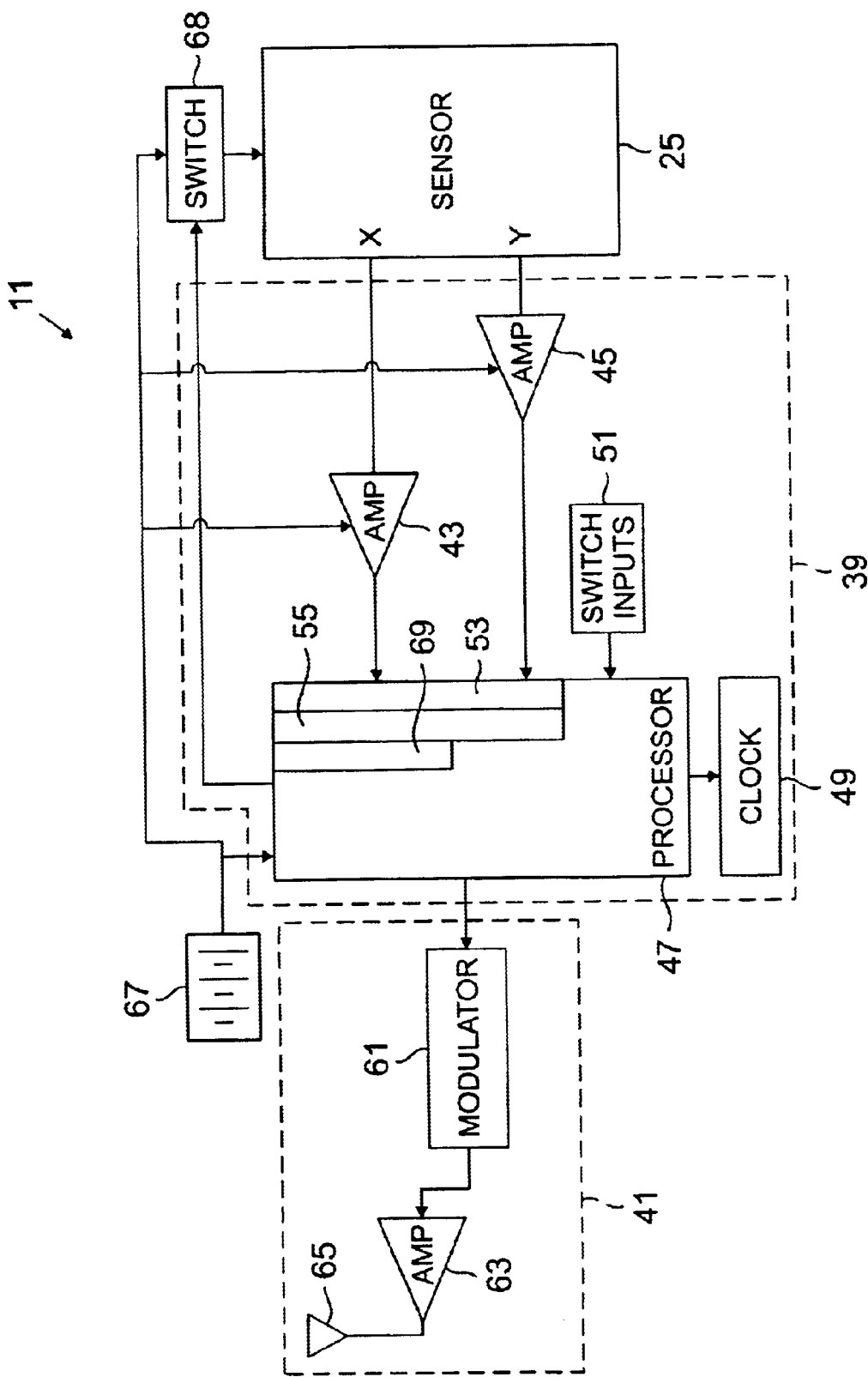
FIG. 2 illustrates a block diagram of the exemplary system set forth with respect to FIG. 1.

Turning next to FIG. 2, there is illustrated a block diagram of the exemplary system of FIG. 1, which includes processing circuitry 39, indicating means 41, power supply 67, and a switch 68, along with sensor 25.

Exemplary processing circuitry 39 illustratively includes a processor 47 and buffer amplifiers 43 and 45 that buffer the analog x and y outputs from sensor 25. Exemplary processor 47, which is associated with sensor 25, is capable of processing the sensed accelerative phenomena as a function of at least one accelerative event characteristic to thereby determine whether an evaluated body movement is within environmental tolerance. Processor 47 also preferably generates state indicia while processing the sensed accelerative phenomena, which may represent the state of the body within the environment over time. Processor 47 is associated with a crystal oscillator/clock 49, switch (DIP) inputs 51, an analog-digital conversion circuitry 53 and a DSP filter 55 (one conventional processor is available from TEXAS INSTRUMENTS, INC., located in Dallas, Tex., United States of America, namely, Model No. MSP430P325).

Exemplary indicating means 41, in response to direction from processor 47, is operable to accomplish at least one of the following: initiate an alarm event; communicate such state, or tolerance, indicia to a monitoring controller; generate statistics; etc. Indicating means 41 may take any number of forms, however, for use in system 11 of the present embodiment, stage 41 is an RF transmitter including RF modulator 61 enabled by processor 47. Exemplary data is presented and modulated at modulator 61, amplified at amplifier 63 and transmitted at antenna 65 (to a remote receiver unit as discussed hereinafter).

According to the present embodiment, power for the various components of system 11 is provided by power supply 67, which illustratively is a 3.6 volt lithium ion battery. Low power management may suitably be under the control of processor 47 utilizing exemplary switched/power supply voltage FET switch 68 at sensor 25, which provides power only during sampling cycles, and operates to shut components down during non-use cycles. For instance, processor 47 may be taken off-line when processing is complete, reducing current drain.

It should be noted that the various circuitry discussed heretofore has been introduced herein for illustrative purposes only. System 11 may be implemented using any suitably arranged computer or other processing system including micro, personal, mini, mainframe or super computers, as well as network combinations of two or more of the same. In point of fact, in one advantageous embodiment, sensor 25 and processor 47 are not co-located, but rather associated wirelessly. To that end, the principles of the present invention may be implemented in any appropriately arranged device having processing circuitry. Processing circuitry may include one or more conventional processors, programmable logic devices, such as programmable array logic ("PALs") and programmable logic arrays ("PLAs"), digital signal processors ("DSPs"), field programmable gate arrays ("FPGAs"), application specific integrated circuits ("ASICs"), large scale integrated circuits ("LSIs"), very large scale integrated circuits ("VLSIs") or the like, to form the various types of circuitry, processors, controllers or systems described and claimed herein.

Conventional computer system architecture is more fully discussed in THE INDISPENSABLE PC HARDWARE BOOK, by Hans-Peter Messmer, Addison Wesley (2nd ed. 1995) and COMPUTER ORGANIZATION AND ARCHITECTURE, by William Stallings, MacMillan Publishing Co. (3rd ed. 1993); conventional computer, or communications, network design is more fully discussed in DATA NETWORK DESIGN, by Darren L. Spohn, McGraw-Hill, Inc. (1993); conventional data communications is more fully discussed in VOICE AND DATA COMMUNICATIONS HANDBOOK, by Bud Bates and Donald Gregory, McGraw-Hill, Inc. (1996), DATA COMMUNICATIONS PRINCIPLES, by R. D. Gitlin, J. F. Hayes and S. B. Weinstein, Plenum Press (1992) and THE IRWIN HANDBOOK OF TELECOMMUNICATIONS, by James Harry Green, Irwin Professional Publishing (2nd ed. 1992); and conventional circuit design is more fully discussed in THE ART OF ELECTRONICS, by Paul Horowitz and Winfield, Cambridge University Press (2nd ed. 1991). Each of the foregoing publications is incorporated herein by reference for all purposes.

Figure 3A:
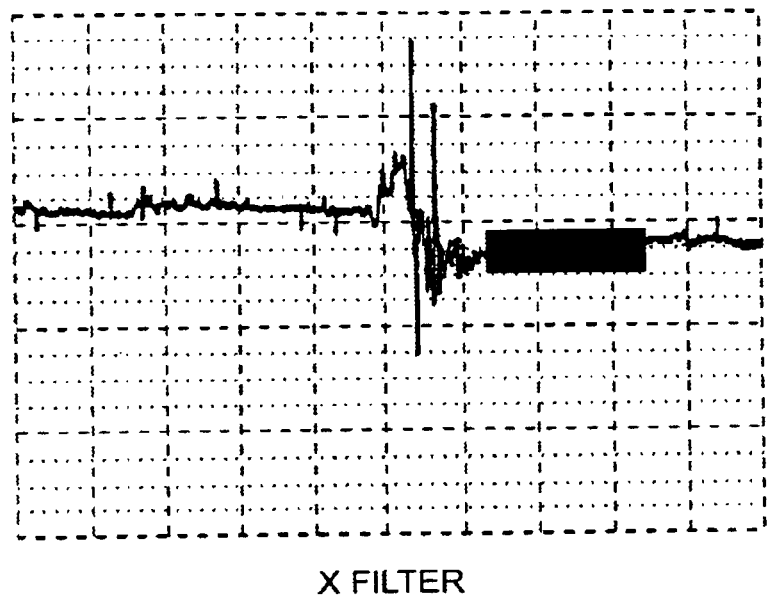
FIGS. 3a to 3d illustrate exemplary strip chart records of output of the sensor introduced in FIGS. 1 and 2 taken during illustrative situations.
Figure 3B:
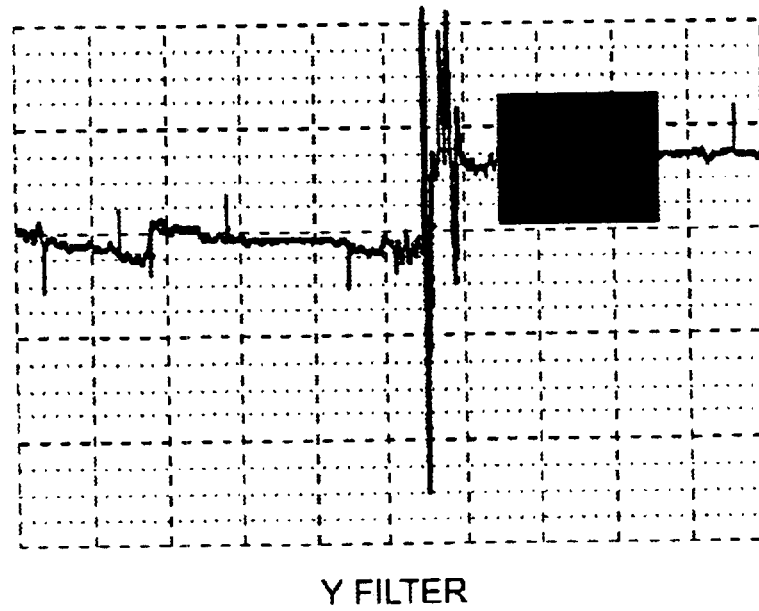
Figure 3C:
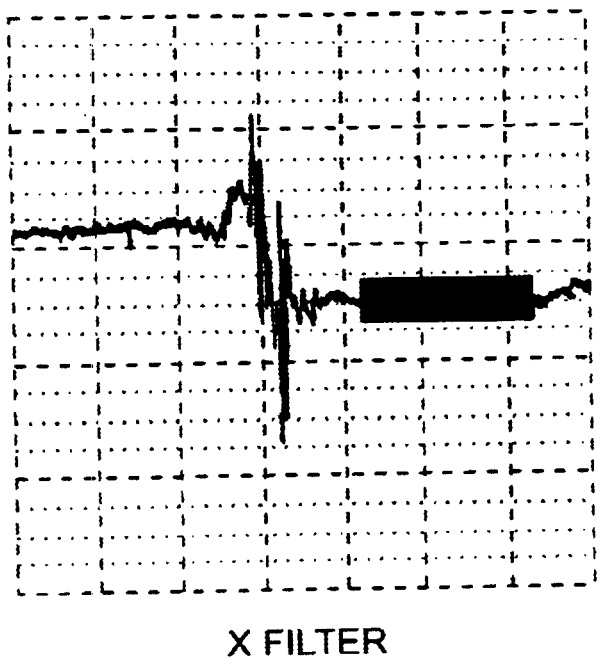
Figure 3D:

Turning next to FIGS. 3a to 3d, illustrated are exemplary strip chart records of output of exemplary sensor 25 of FIGS. 1 and 2 taken during illustrative situations. More particularly, FIGS. 3a and 3b illustrate the analog signal at the x and y outputs of sensor 25 during a fall by a body to the left, and whereas FIGS. 3c and 3d illustrate the analog signal at the x and y outputs of sensor 25 during a fall by a body to the right (the dark blocks indicating an alarm condition). As can be seen from the exemplary traces, a fall to the left and to the right are both distinguishable by the disruption of a stable position, or normal body movement, by a concussive force followed by a distinctly different ending stable position. According to the illustrative embodiment introduced herein, the direction of fall is clear from the position of the ending trace at the y outputs. If the fall had been more forward or backward, the x output traces would likewise clearly indicate the same (this assumes x and y sensor axes orientation as set forth in FIG. 1). Of course, the same x and y outputs of the sensor 25 may be suitably processed to simply determine position of the body, for instance, such as when a person is lying down, when a box has tipped over, etc.

Figure 4:
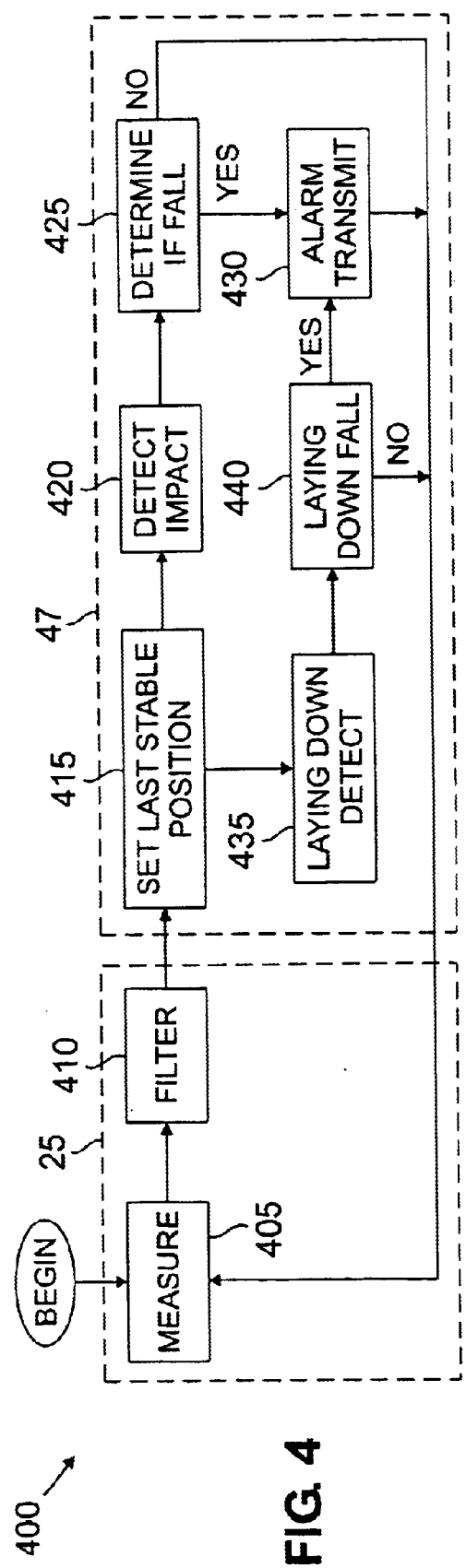
FIG. 4 illustrates an operational flow diagram of an exemplary method of programming a processor in accordance with a fall detection application of the principles of the present invention.

Turning next to FIG. 4, illustrated is operational flow diagram of an exemplary method (generally designated 400) of programming of processor 47 in accordance with a fall detection application of the principles of the present invention. For the purposes of illustration, concurrent reference is made to system 11 of FIGS. 1 and 2. It should be noted that this illustration introduces an exemplary operational method for programming processor 47 for its use as a fall detector, and that suitable alternate embodiments of system 11 for evaluating movement of a body relative to different environments may likewise be implemented in accordance with the principles hereof, such as for relative position, other assistance monitoring, transparent monitoring, tactical maneuver monitoring etc.

Exemplary method 400 begins and a request for sampling measurements is generated, likely by processor 47 (Step 405), either in response to an executing operations program or upon initiation by a user, possibly remotely from a monitoring controller (discussed with reference to FIG. 8). Sensor 25 sense x and y acceleration values generating measurement signals at the outputs at sensor 25.

In the present implementation, the measurement signals are converted from analog to digital format and filtered by filter 55 (Step 410; thereby reducing probability that an out-of-tolerance abnormal movement will be determined incorrectly in response to a single sharp impact such as a collision between mount 17 and a hard surface when sensor 25 is off the body causing a sharp signal spike).

Processor 47 uses dc voltage components of the outputs from sensor 25 to determine a last stable position of the body on which sensor 25 is mounted (Step 415). More particularly, processor 47 repeatedly compares successive input values with immediately preceding input values and, if within tolerance, are added thereto and stored in an accumulator. This is repeated until Z samples have been accumulated and added over some defined period of time (e.g., one second) or until a received input is out of tolerance, in which case the sampling cycle is reinitiated. When Z samples are accumulated and added, the accumulated value is divided by Z to determine a "last stable" static acceleration average value, which is saved and is indicative of the last stable position of the body. Sampling and/or sampling cycle rates may be varied, but, while preferably not continuous due to power consumption concerns, should be substantially continual. It is important to note, therefore, that such characteristics maybe statically maintained or dynamically generated.

Processor 47 uses ac voltage components of each output from sensor 25 to check against a G force threshold value set at DIP switch 51 to see if it exceeds the threshold (Step 420;

thus qualifying as a potential fall impact, in the current example, possibly an intensity in excess of about 2 to 4 G depending upon desired sensitivity). According to the present implementation, if three of these dynamic acceleration measurements are received in excess of the threshold without five intervening measurements that are less than the threshold, the impact detect flag may be set.

Processor 47 determines a fall by testing a post-impact stream of samples against a tolerance (Step 425; for instance, a selected value of the ac voltage components, for example a value less than about 2 G). Each new sample is tested against the previous sample to see if the position of the body has stabilized. When the position has stabilized to less than the tolerance, W samples are averaged to get the new stable static acceleration average value corresponding to the new stable position.

Processor 47, in response to the value corresponding to the new stable position is shifted indicating a change of body position of 45° or more from the last stable position, classifies the event as a debilitating fall and alert stage 41 is activated (Step 430). A greater stabilization or post-stabilization sample period may be selected to allow more time for an uninjured user to rise without issuance of an alert.

Processor 47, after setting the last stable position, adds the absolute values of the x and y last stable positions together, and, then determines whether the body associated with sensor 25 is lying down if the added value exceeds a value corresponding to 90° plus or minus 25% (Step 435). In such case, after a selected time (for example, four seconds) with repeated like values, the laying down detect flag is set. While this flag is set, any impact that exceeds the G force threshold is treated as a debilitating fall (Step 440). The flag is set only as long as the added value continues to indicate that the wearer is laying down.

It should be noted that the foregoing embodiment was introduced for illustrative purposes only and that the present invention broadly introduces systems, as well as methods of operating such systems, that evaluate movement of a body relative to an environment, which in the above-given example is an assistance monitoring environment. An important aspect of the present invention is that processor 47 is operable to process sensed accelerative phenomena as a function of at least one accelerative event characteristic, and that such characteristics will largely be defined by the specific application. Therefore, system 11, and, more particularly, processor 47, generates state indicia relative the environment of interest, and determines whether the evaluated body movement is within tolerance in the context of that environment. For instance, "tolerance" would likely be very different for a monitored body of an elderly person with a heart condition, a toddler, a box in a freight car, a container of combustible gas, etc.

Figure 5:
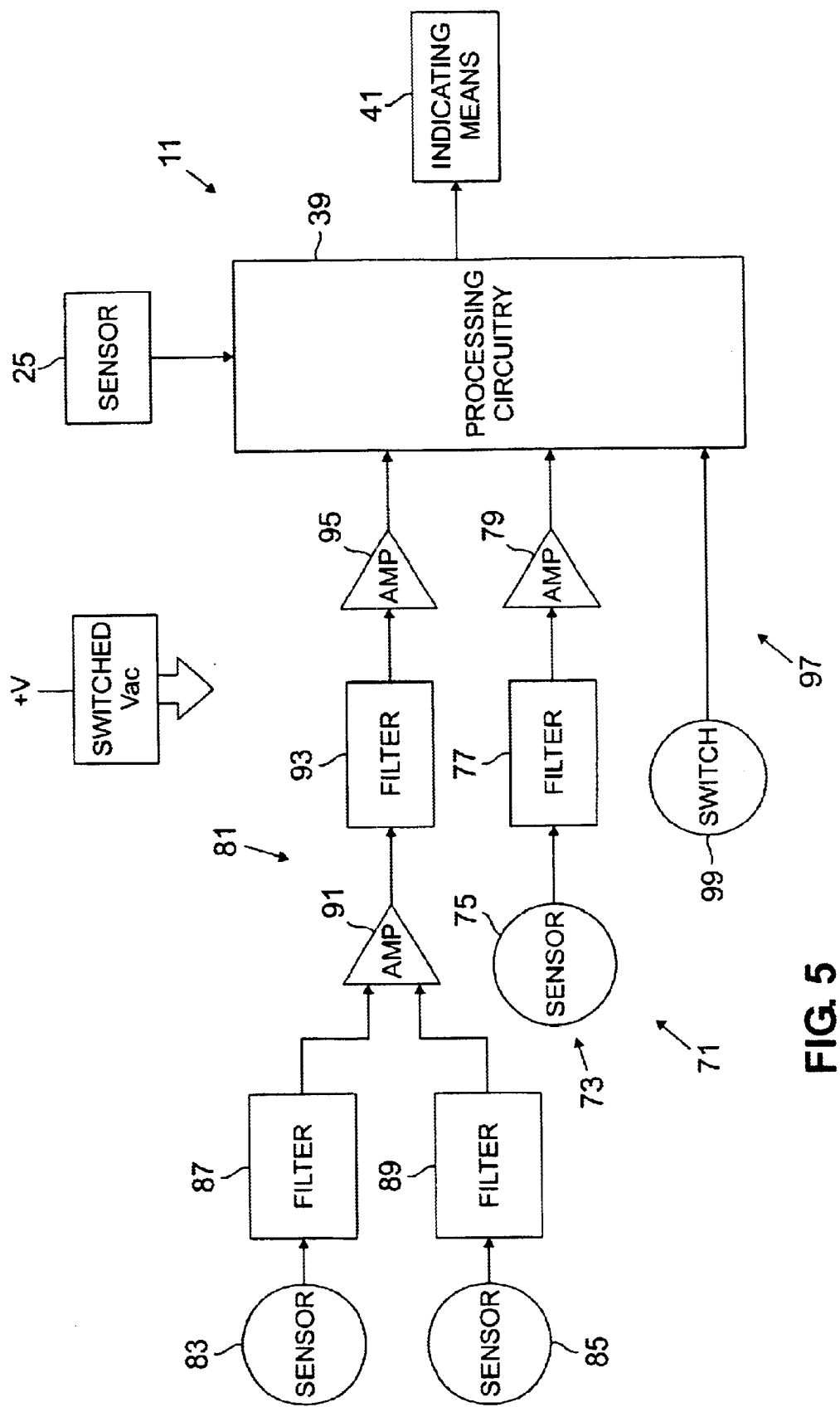
FIG. 5 illustrates a functional block diagram of an alternate sensing system that may suitably be associated with the processor of the present invention.

Turning next to FIG. 5, illustrated is a functional block diagram of an alternate sensing system (generally designated 71) that may suitably be associated with processor 47 of FIGS. 1, 2, and 4 in accordance with the principles of the present invention. In this embodiment, components utilizable with system 11 are configured again as a human fall monitor/detector, and any or all of these additional monitoring functions may be employed with system 11. For purposes of illustration, concurrent reference is made to processor 47 of FIGS. 2 and 4.

Exemplary sensor 71 includes a respiration module 73, which includes a body contact breath sensor 75 (for example a volumetric sensor, or a near body breath sensor), low pass filter 77 and amplifier 79 providing output signals indicative of respiration rate and vitality to processor 47. The outputs are processed and, when a dangerous respiratory condition is suggested (generates state indicia relative the environment, and determines whether the evaluated body movement (broadly defined herein to include organic physiologic phenomena) is within environmental tolerance), an identifiable (for example, by signal coding) alarm sent indicating means 41.

Sensor 71 further includes an ECG module 81, which includes input electrodes 83 and 85 providing heart rate signals to filters 87 and 89. The filtered signals are amplified at amplifier 91 and band pass filtered at filter 93. The output is amplified at 95 for input to processor 47 and processed so that dangerous heart rhythms and events can be detected (generates state indicia relative the environment, and determines whether the evaluated body movement is within environmental tolerance) and an identifiable alarm sent at alert stage 41.

Sensor 71 further includes a panic button module 97 that is operable using a standard user activated switch 99 positioned at housing 17 allowing a user to initiate a call for help. The switch output is input to processor 47 to initiate an identifiable alarm at alert stage 41.

Figure 6:
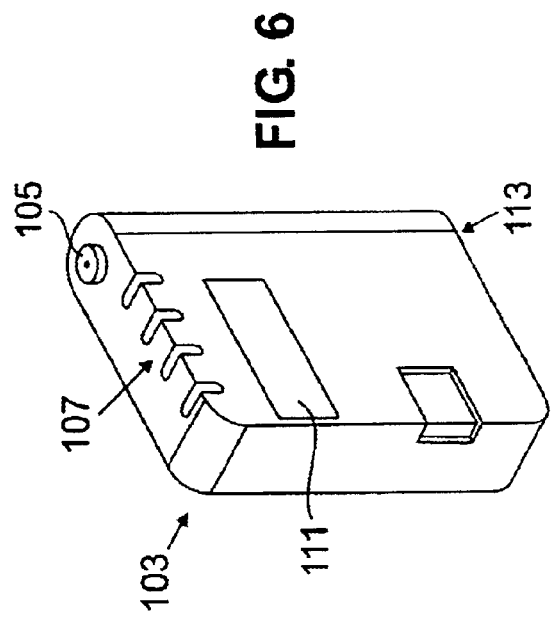
FIG. 6 illustrates a perspective view of an exemplary remote receiver unit of the system of this invention.
Figure 7:
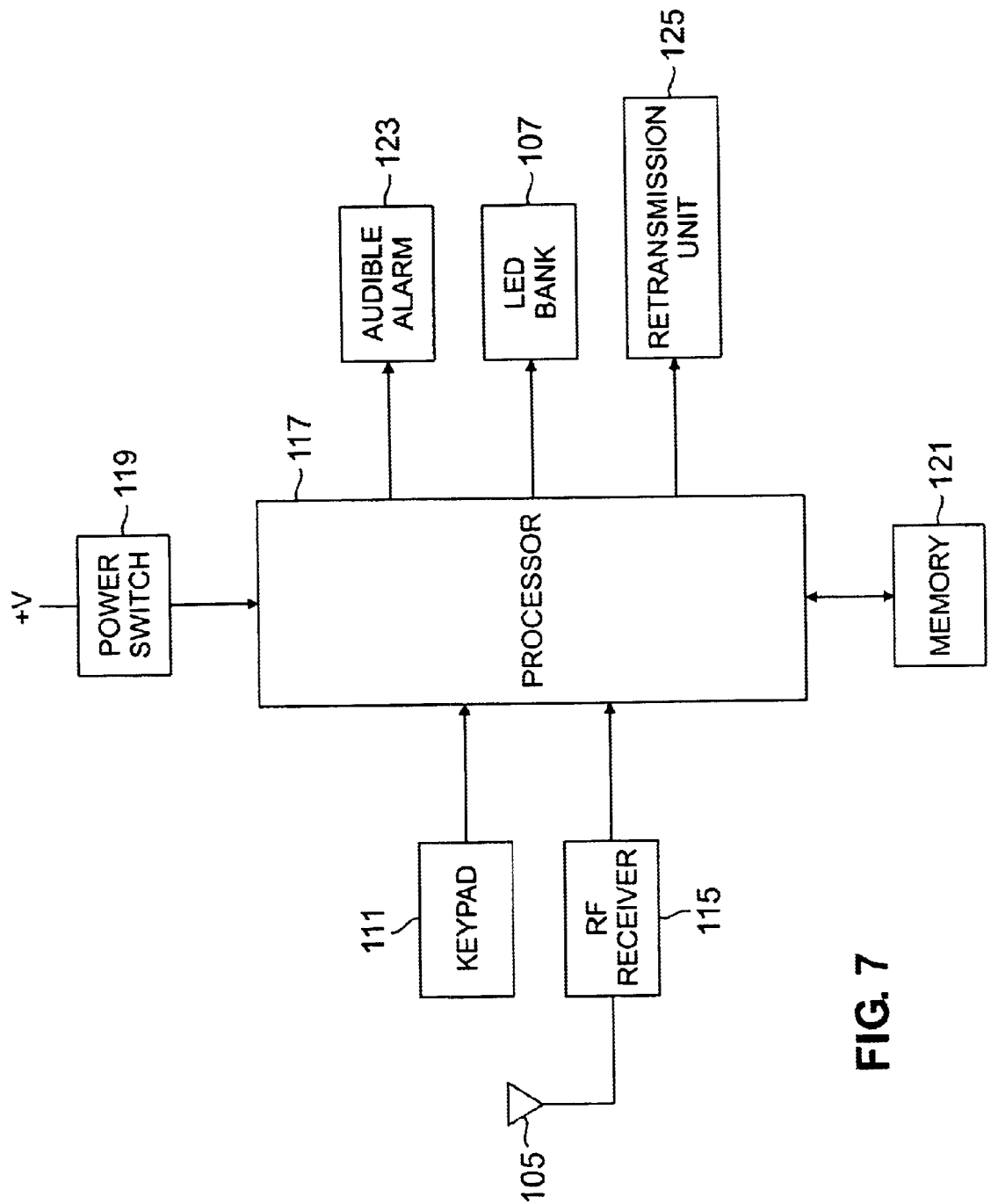
FIG. 7 illustrates a functional block diagram of the exemplary receiver unit of FIG. 6.

Turning momentarily to FIGS. 6 and 7, illustrated are a perspective view of an exemplary remote receiver unit of the system of this invention and a functional block diagram of the same. In a distributed system in accord with one embodiment of this invention, a remote receiver unit 103. (for example a wall mountable unit) as shown in FIGS. 6 and 7 is provided for receipt of transmissions from sensor 25 and/or system 71. Unit 103 includes a receiver antenna 105, indicator LED's 107 (including indicators for as many detector functions as are employed in the specific embodiment of the apparatus being monitored, as well as an indicator for unit on/off status), and a user interface input keypad 111 for unit setup, reset and alarm deactivation. Power access 113 is provided at the bottom of the unit.

RF receiver 115 is tuned to receive alarm transmissions from sensor 11/71 and-presents the signal received for processing at processor 117 for alarm identification and appropriate output. Processor 117 also receives inputs from keypad 111 and power switch 119. Non-volatile memory 121 is provided for input of identification of the user and/or of the apparatus being monitored. Audible alarm 123, LED bank 107 and retransmission unit 125 (an autodialer, imbedded digital cellular technology, RF transmitter, an Internet appliance, or the like) are connected to receive outputs from processor 117.

When a transmission is received, or when battery power at the body mounted apparatus is low, an audible alarm is sounded and the appropriate LED (indicative of the condition causing the alarm, for example a debilitating fall by a user of apparatus 11) is activated. If not disabled by the user at key pad 111 within a short period, processor 117 activates retransmission unit 125 initiating a call for help or other remote notification.

Operational setup of unit 103 is also accomplished under programming at processor 117 and by sequential operation by a user or technician of keypad 111 and/or power switch 119 as is known (including user ID set, learn mode operations, reset or reprogramming operations, and urgency code operations).

Figure 8:
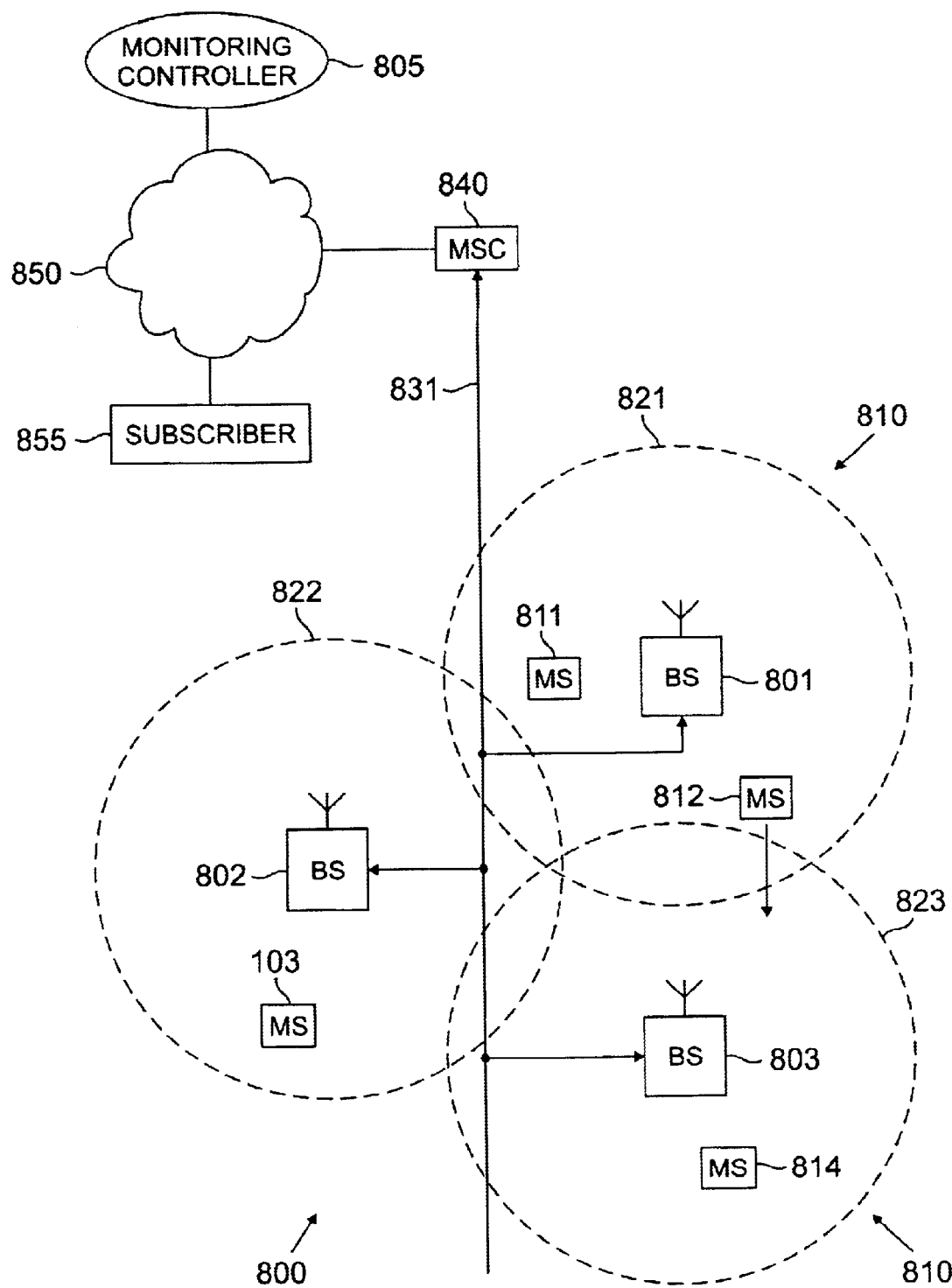
FIG. 8 illustrates an exemplary wireless network that is associated via a wired network, such as the Internet, to a remote monitoring controller according to one embodiment of the present invention.

Turning next to FIG. 8, illustrated is an exemplary hybrid wireless/wired network (generally designated 800) that is associated with a remote monitoring controller 805 according to one embodiment of the present invention. The wireless network 810 is introduced for illustrative purposes only, and comprises a plurality of cell sites 821 to 823, each containing one of the base stations, BS 801, BS 802, or BS 803. Base stations 801 to 803 are operable to communicate with a plurality of mobile stations (MS) including MS 103 (remote receiver unit 103), and MS 811, MS 812 and MS 814. Mobile stations MS 103, and MS 811, MS 812 and MS 814, may be any suitable cellular devices, including conventional cellular telephones, PCS handset devices, portable computers, metering devices, transceivers, and the like (including, for instance, remote receiver unit 103).

Dotted lines show the approximate boundaries of the cell sites 821 to 823 in which base stations 801 to 803 are located. The cell sites are shown approximately circular for the purposes of illustration and explanation only. It should be clearly understood that the cell sites also may have irregular shapes, depending on the cell configuration selected and natural and man-made obstructions.

In one embodiment of the present invention, BS 801, BS 802, and BS 803 may comprise a base station controller (BSC) and a base transceiver station (BTS). Base station controllers and base transceiver stations are well known to those skilled in the art. A base station controller is a device that manages wireless communications resources, including the base transceiver station, for specified cells within a wireless communications network. A base transceiver station comprises the RF transceivers, antennas, and other electrical equipment located in each cell site. This equipment may include air conditioning units, heating units, electrical supplies, telephone line interfaces, and RF transmitters and RF receivers, as well as call processing circuitry. For the purpose of simplicity and clarity in explaining the operation of the present invention, the base transceiver station in each of cells 821, 822, and 823 and the base station controller associated with each base transceiver station are collectively represented by BS 801, BS 802 and BS 803, respectively.

BS 801, BS 802 and BS 803 transfer voice and data signals between each other and the public telephone system (not shown) via communications line 831 and mobile switching center (MSC) 840. Mobile switching center 840 is well known to those skilled in the art. Mobile switching center 840 is a switching device that provides services and coordination between the subscribers in a wireless network and external networks 850, such as the Internet, public telephone system, etc. Communications line 831 may be any suitable connection means, including a T1 line, a T3 line, a fiber optic link, a network backbone connection, and the like. In some embodiments of the present invention, communications line 831 may be several different data links, where each data link couples one of BS 801, BS 802, or BS 803 to MSC 840.

In the exemplary wireless network 800, MS 811 is located in cell site 821 and is in communication with BS 801, MS 103 is located in cell site 822 and is in communication with BS 802, and MS 814 is located in cell site 823 and is in communication with BS 803. MS 812 is also located in cell site 821, close to the edge of cell site 823. The direction arrow proximate MS 812 indicates the movement of MS 812 towards cell site 823.

For the purposes of illustration, it is assumed that system 11 is associated with an elderly person whose residence is wirelessly monitored. It is further assumed that sensor 25 is associated with the elderly person and that processor 47 is coupled in MS/remote receiver unit 103, such that sensor 25 and processor 47 are wirelessly associated.

System 11 repeatedly senses various physiological phenomena of the elderly person, including accelerative phenomena of his body. Remote processor 47 processes the repeatedly sensed phenomena, and, particularly, the accelerative phenomena of the body, as a function of at least one accelerative event characteristic to thereby determine whether the evaluated body movement is within environmental tolerance. Processor 47 advantageously generates state indicia while processing the sensed accelerative phenomena, representing the state of the body within the environment over time.

Exemplary processor 47 is programmed to distinguish between normal and abnormal accelerative events (e.g., walking, sitting, lying down, etc. versus tripping, falling down, etc.), and, when an abnormal event is identified, indicates whether the abnormal event is tolerable, or within tolerance. Processor 47 may also suitably be programmed to distinguish other physical characteristics, including temperature, pressure, force, sound, light, relative position (including lying down), and the like.

As processor 47 generates state indicia, which includes tolerance indicia, it uses the same to determine whether the evaluated body movement is within environmental tolerance. Preferably, such tolerance indicia is compared with at least one threshold, likely associated with the accelerative event characteristic. In response to such comparison, processor 47 controls a suitable indicating means to initiate an alarm event (locally and via network 810 to monitoring controller 805), to communicate such tolerance indicia to a monitoring controller 805, to generate statistics (locally and via network 810 to monitoring controller 805), or the like.

According to a related preferred embodiment, such state indicia, and other information is communicated from time to time to monitoring controller 805, from which such information may suitably be perceived. For instance, a technician, medical professional, or relative might wish to review the activities and status of the elderly person. This may easily be facilitated via a centralized data repository accessible via the Internet, or via any other suitably arranged network. While viewing such information, the technician, medical professional, or relative (subscriber 2, generally designated 855) might initiate a diagnostic equipment check, a physiological test, a simple status check, or the like. Similarly, monitoring controller 805, via the network 800, may monitor a "heartbeat" signal generated periodically by MS/remote receiver unit 103, the heartbeat indicating that unit 103 is functional.

Figure 9:
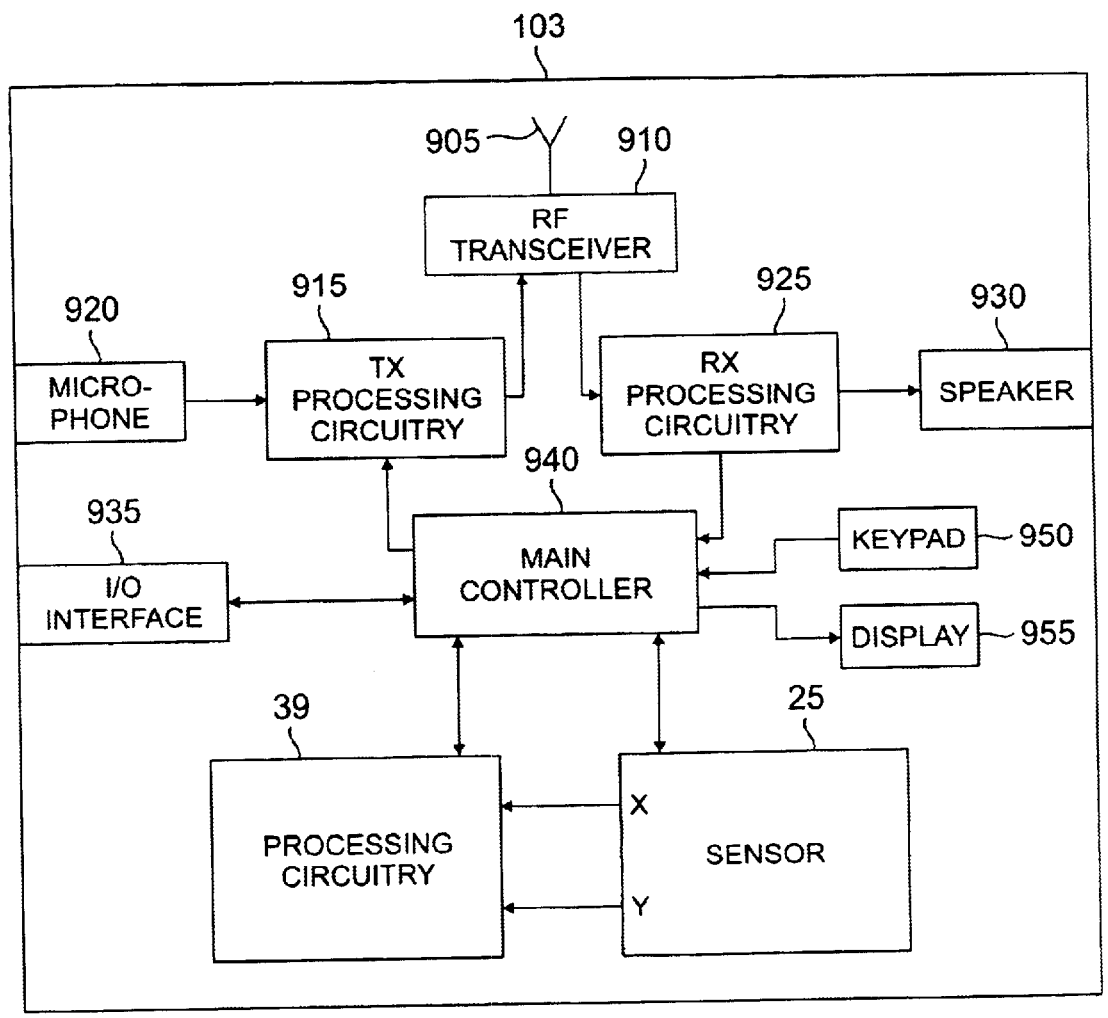
FIG. 9 illustrates an exemplary communications device that contains an exemplary embodiment of the system of the present invention for evaluating body movement.

FIG. 9 is a block diagram illustrating how the circuitry of the present invention may utilized within an exemplary communications device. The exemplary communications device shown is wireless mobile station/remote receiver unit 103. The MS designation has been dropped for convenience. Remote receiver unit 103 comprises radio frequency (RF) transceiver 910 coupled to antenna 905 for receiving a forward channel signal from wireless network base station BS 802 and for sending a reverse channel signal to wireless network base station BS 802 in accordance with well known principles.

RF transceiver 910 is coupled to receiving processing circuitry 925 which, in turn, is coupled to speaker 930 and main controller 940. Main controller 940 is coupled to transmission processing circuitry 915 which, in turn, is coupled to microphone 920 and RF transceiver 910. Main controller 940 controls the reception of forward channel signals and the transmission of reverse channel signals in accordance with well known principles. Main controller 940 is also coupled to I/O interface 935, keypad 950 and display unit 955. Main controller 940 controls the transmission of signals to and from these elements with methods well known in the art.

Sensor 25 is coupled to main controller 940. Precessing circuitry 39 comprising processor 47 (not shown in FIG. 9) is also coupled to main comptroller 940. The x output signal of sensor 25 and they output signal of sensor 25 are coupled to processing circuitry 39 as previously described. In this embodiment of the present invention, the structure of indicating means 41 (not shown in FIG. 9) comprises transmit processing circuitry 915, RF transceiver 910 and antenna 905.

When sensor 25 detects a body movement that signifies the occurrence of a potentially dangerous event (e.g., a fall), processing circuitry 39 immediately causes main controller 940 to send an alarm via transmit processing circuitry 915, RF transceiver 910 and antenna 905. The alarm signal may also include detailed information concerning the values of the measured x and y signals.

In an alternate embodiment of the present invention, processing circuitry 39 comprising processor 47 (not shown in FIG. 9) is capable of recording the values of the measured x and y signals and recording the times of the measurements using time signals from clock 49 (not shown in FIG. 9). In some cases it will be more practical to record the values of the x and y signals for later downloading that to immediately transmit an alarm signal and the values of the x and y signals. For example, when a shipping container is allowed to tip over or is otherwise mishandled during shipment, it may not be practical to immediately respond to the mishandling event. At the conclusion of the shipment, however, the time that the mishandling event occurred may be recovered from processing circuitry 39. The time of the mishandling event may then be compared to the shipping schedule to determine the identity of the individual carrier responsible for the mishandling event.

In an alternate embodiment of the present invention, sensor 25 may comprise tilt switch sensors of the type described in U.S. patent application Ser. No. 09/542,197 filed Apr. 4, 2000 by Halleck et al. entitled "Apparatus and Method for Detecting An Inclination of A Body."

Although the present invention has been described in detail, those skilled in the art should understand that they can make various changes, substitutions and alterations herein without departing from the spirit and scope of the invention in its broadest form.

What is claimed is:

1. A system within a communications device capable of evaluating movement of a body relative to an environment, said system comprising:
    a sensor, associable with said body, that senses dynamic and static accelerative phenomena of said body, and
    a processor, associated with said sensor, that processes said sensed dynamic and static accelerative phenomena as a function of at least one accelerative event characteristic to thereby determine whether said evaluated body movement is within environmental tolerance
    wherein said processor generates tolerance indicia in response to said determination; and
    wherein said communication device transmits said tolerance indicia.

2. The system as claimed in claim 1 wherein said communications device comprises one of: a cordless telephone, a cellular telephone and a personal digital assistant.

3. The system as claimed in claim 1 wherein said communications device comprises one of: a hand held computer, a laptop computer and a wireless Internet access device.

4. The system claimed in claim 1 wherein said communications device transmits an alarm signal when said processor determines that an evaluated body movement signifies an occurrence of a potentially dangerous event.

5. The system as claimed in claim 4 wherein said alarm signal comprises a measured value of an x output signal of said sensor and a measured value of a y output signal of said sensor.

6. The system as claimed in claim 4 wherein said potentially dangerous event occurs when said body falls.

7. The system as claimed in claim 4 wherein said communications device transmits said alarm signal through one of: a wired network and a wireless network.

8. The method as claimed in claim 4 wherein said communications device transmits said alarm signal through a portion of the Internet.

9. The system as claimed in claim 1 wherein said communications device transmits said tolerance indicia to a monitoring controller.

10. A method for operating a system within a communications device, wherein said system is capable of evaluating movement of a body relative to an environment, wherein said system comprises a sensor, associable with said body, that senses dynamic and static accelerative phenomena of said body, and
    a processor, associated with said sensor, that processes said sensed dynamic and static accelerative phenomena as a function of at least one accelerative event characteristic to thereby determine whether said evaluated body movement is within environmental tolerance, wherein said method comprises the steps of:
    generating tolerance indicia in said processor in response to said determination of whether said evaluated body movement is within said environmental tolerance; and
    transmitting said tolerance indicia through said communications device.

11. The method as claimed in claim 10 wherein said communications device comprises one of: a cordless telephone, a cellular telephone and a personal digital assistant.

12. The method as claimed in claim 10 wherein said communications device comprises one of: a hand held computer, a laptop computer and a wireless Internet access device.

13. The method claimed in claim 10 further comprising the step of:
    transmitting an alarm signal through said communications device when said processor determines that an evaluated body movement signifies an occurrence of a potentially dangerous event.

14. The method as claimed in claim 13 wherein said alarm signal comprises a measured value of an x output signal of said sensor and a measured value of a y output signal of said sensor.

15. The method as claimed in claim 13 wherein said potentially dangerous event occurs when said body falls.

16. The method as claimed in claim 13 further comprising the step of:
    transmitting said alarm signal from said communications device through one of: a wired network and a wireless network.

17. The method as claimed in claim 13 further comprising the step of: transmitting said alarm signal from said communications device through a portion of the Internet.

18. The method as claimed in claim 10 further comprising the step of: transmitting said tolerance indicia from said communications device to a monitoring controller.

19. The method as claimed in clam 10 further comprising the steps of:

generating in said processor state indicia while processing said sensed accelerative phenomena, which represents a state of said body within said environment over time; and transmitting said state indicia through said communications device.

20. The method as claimed in claim 10 further comprising the steps of:

generating in said processor an output signal that is indicative of measurements of both static and dynamic acceleration of said body in plural axes; and transmitting said output signal through said communications device.

* * * * *

UNITED STATES PATENT AND TRADEMARK OFFICE
Certificate

Patent No. 6,864,796 B2                                                                Patented: March 8, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael L. Lehrman, Washington, DC (US); Alan R. Owens, Longmont, CO (US); Michael E. Halleck, Longmont, CO (US); Edward L. Massman, Dallas, TX (US); and Michael D. Halleck, Brighton, CO (US).

Signed and Sealed this Twenty-seventh Day of May 2014.

<div style="text-align:right">

HAI PHAN
*Supervisory Patent Examiner*
Art Unit 2685
Technology Center 2600

</div>